United States Patent

Haning et al.

[11] Patent Number: 6,042,619
[45] Date of Patent: Mar. 28, 2000

[54] COMPOSITIONS FOR TEMPORARILY COLORING THE HAIR

[75] Inventors: Linda J. Haning, Prior Lake; Pamela A. Helms, Minnetonka; Coreen Ann Johnson, Inver Grove Heights, all of Minn.

[73] Assignee: Bristol-Myers Squibb Co., New York, N.Y.

[21] Appl. No.: 08/950,855

[22] Filed: Oct. 13, 1997

Related U.S. Application Data

[63] Continuation of application No. 08/532,175, Sep. 22, 1995, Pat. No. 5,679,114.

[51] Int. Cl.[7] ..................................................... A61K 7/06
[52] U.S. Cl. ..................... 8/405; 8/554; 8/581; 8/637.1; 424/70.6; 424/70.12
[58] Field of Search ............................ 8/405, 435, 554, 8/581, 606, 637.1, 931, DIG. 1; 424/70.6, 70.11, 70.12

[56] References Cited

U.S. PATENT DOCUMENTS

| | | | |
|---|---|---|---|
| 4,183,366 | 1/1980 | Bartuska et al. | 132/7 |
| 4,559,057 | 12/1985 | Bogaty et al. | 8/554 |
| 4,581,230 | 4/1986 | Grollier et al. | 424/74 |
| 4,719,099 | 1/1988 | Grollier et al. | 8/406 |
| 4,871,536 | 10/1989 | Arrandeau et al. | 424/59 |
| 4,873,079 | 10/1989 | Hahn | 424/70.6 |
| 4,938,954 | 7/1990 | Gross et al. | 424/70.1 |
| 4,992,077 | 2/1991 | Tennigkeit et al. | 8/406 |
| 4,994,088 | 2/1991 | Ando et al. | 8/405 |
| 5,006,127 | 4/1991 | Tennigkeit et al. | 8/406 |
| 5,205,837 | 4/1993 | Andrean et al. | 8/405 |
| 5,330,747 | 7/1994 | Krzysik | 424/63 |
| 5,439,682 | 8/1995 | Wivell et al. | 424/70.21 |
| 5,445,823 | 8/1995 | Hall et al. | 424/401 |
| 5,470,884 | 11/1995 | Corless et al. | 514/714 |
| 5,476,660 | 12/1995 | Somasundaran et al. | 424/401 |
| 5,700,452 | 12/1997 | Deckner et al. | 424/59 |

FOREIGN PATENT DOCUMENTS

| | | |
|---|---|---|
| 5-331780 | 12/1993 | Japan . |
| 2149806 | 6/1985 | United Kingdom . |
| 2260985 | 5/1993 | United Kingdom . |

OTHER PUBLICATIONS

English language translation of JP 5–331,780, Sanyo Shikiso Co, pp. 1–18. Dec. 1993.

*Primary Examiner*—Caroline D. Liott
*Attorney, Agent, or Firm*—Charles J. Zeller

[57] ABSTRACT

A hair treatment composition for temporarily coloring the hair is disclosed. A polymer having repeating units of $\{-CH_2(CH_3)C[CO_2(CH_2)_2N^+(CH_3)_3X^-]-\}_n$; wherein n has a value of about 25 to 1,000 and X is an anion, and a metal containing pigment are combined. The resultant product is applied to the hair to effect temporary coloring of the hair.

5 Claims, No Drawings

US 6,042,619

COMPOSITIONS FOR TEMPORARILY COLORING THE HAIR

This application is a continuation of, and claims the benefit of Ser. No. 08/532,175; filed Sep. 22, 1995; now U.S. Pat. No. 5,679,114.

BACKGROUND OF THE INVENTION

1. Field of the Invention

The present invention deals with hair care products. In particular, the present invention deals with hair care products employed to color the hair, and particularly products to temporarily color the hair.

2. Description of the Art Practices

Various products are known for use in permanently coloring the hair. A major problem in coloring of the hair is that the user of the product often does not care for the color after it has been applied. The use of permanent hair colors may also prevent the user from wearing certain items of the wardrobe which conflict with the newly selected and applied hair color. When the prospective user of the hair color merely wants to determine how the hair color will appear, the use of a permanent product is not desirable.

The reader is directed to the following references for the general discussion of hair care products. U.S. Pat. No. 4,992,077 issued Feb. 12, 1991 to Tennigkeit, et. al., discusses the use of oxidative dyes in a creme or gel form. Tennigkeit, in U.S. Pat. No. 5,006,127, issued Apr. 9, 1991 further discusses oxidative dyes in creme or gel form.

Bartuska, in U.S. Pat. No. 4,183,366 issued Jan. 15, 1980, discusses henna-based hair coloring and/or hair conditioning compositions. The compositions of Bartuska are stated to contain non-ionic surface active agents, water soluble polymers, and quaternary salts.

Andrean, in U.S. Pat. No. 5,205,837, issued Apr. 27, 1993, describes powder form products containing at least one synthetic melanotic pigment formed in situ by oxidation of an indole compound. The Andrean products are stated to be for use in dyeing hair.

Gross, et. al., in U.S. Pat. No. 4,938,954, issued Jul. 3, 1990, describes hair wax compositions containing polyethylene glycol, a hydrogenated castor oil which is ethoxylated, glycerol or ethyl hexane diol, and/or a lower molecular weight polyethylene glycol, and water.

Hahn, in U.S. Pat. No. 4,873,079, issued Oct. 10, 1989, describes temporary or semipermanent hair coloring compositions. The compositions of Hahn are stated to comprise an aqueous vehicle having a hair coloring component. The compositions of Hahn are stated to further include a co-solvent for the hair colorant which is a diol selected from a group consisting of aliphatic hydrocarbon diols having from 5 to 8 carbon atoms and bis-(hydroxy-alkyl) cyclo hexanes having from 7 to 14 carbon atoms.

United Kingdom patent application 2 149 806 A to Nakumura, which published Jun. 19, 1985 describes in hair coloring compositions comprising colored mica, and optionally iron oxide powder, and a silicone oil. The Nakumura United Kingdom patent optionally includes a propellant.

The present invention deals with hair color products which are temporary in nature yet which provide a natural coloring to the hair. By temporary it is meant that the color added to the hair will wash out upon shampooing the hair.

To the extent that the foregoing references are applicable to the present invention they are herein specifically incorporated by reference. Throughout the specification and claims, percentages and ratios are by weight unless otherwise indicated. Temperatures given herein are degrees Celsius unless otherwise indicated.

SUMMARY OF THE INVENTION

The present invention describes a hair treatment composition comprising:

a. a polymer having repeating units of:
$\{-CH_2(CH_3)C[CO_2(CH_2)_2N^+(CH_3)_3X^-]-\}_n$; and, b. a metal containing pigment, wherein n has a value of about 25 to 1,000 and X is an anion.

The present invention also describes a hair treatment composition comprising:

a. a polymer having repeating units of:
$\{-CH_2(CH_3)C[CO_2(CH_2)_2N^+(CH_3)_3Cl^-]-\}_n$; and, b. a metal oxide coated mica where the metal source is a member selected from the group consisting of iron and titanium provided further that the metal oxide coated mica has a mean particle size distribution of about 5 to about 100 microns, c. cyclomethicone; and, d. water; and, provided further n has a value of about 25 to 1,000.

The present invention also describes a method of treating hair to temporarily color the hair including the steps of contacting the hair with a composition:

a. a polymer having repeating units of:
$\{-CH_2(CH_3)C[CO_2(CH_2)_2N^+(CH_3)_3X^-]-\}_n$; and, b. a metal containing pigment, and water, for a time sufficient to impart a color to the hair, provided further that n has a value of about 25 to 1,000 and X is an anion.

DETAILED DESCRIPTION OF THE INVENTION

The first component to be discussed in the present invention is a polymer component. The polymer component is particularly important to the present invention in that it allows suspension of the metal containing pigment.

The use of the particular polymer in the present invention is highly advantageous in that it avoids pilling upon application of the hair treatment composition onto the hair. Pilling is the phenomena analogous to the fuzzy balls found on cotton or woolen sweaters. The avoidance of pills (agglomerates) is particularly important to the present invention.

The polymer of the present invention has the formula as shown in the Summary of the Invention. The polymer is obtained from Allied Colloids, Inc., Post Office Box 820, 2301 Wilroy Road, Suffolk, Va. The preferred polymer for use in the present invention is obtained as Salcare SC 96™, a liquid dispersion polymer composition.

The composition of the Salcare SC 96T product is approximately 44% by weight Polyquaternium 37 polymer. The Polyquaternium 37 polymer is a water swellable polymer and is also referred to as N,N,N-trimethyl-2-[methyl-1-oxo-2-propenyl]oxy]ethanaminium chloride homopolymer or N,N,N-trimethyl-2-(methyl-1-oxo-2-propenyloxy] chloride homopolymer. The remainder of the Salcare SC 96™ polymer composition is described as comprising a mixture of propylene glycol/dicaprylate/dicaprate 50%, polypropyleneglycol-1 trideceth 6 at 6%.

The preferred polymer composition of the present invention at a 3% active weight in water (97%) has a Brookfield viscosity of 100,000. The preferred polymer composition supplied at 2% active by weight (98% water) has a viscosity maximum at approximately pH 4.0. The viscosity of the preferred polymer composition decreases significantly at pH 2 and below. The preferred polymer composition at a 2% active concentration to pH 8 decreases in viscosity. The preferred polymer is water-swellable and not water-soluble.

The polymer per se is utilized in the present invention at about 0.5 to about 5% by weight. Preferably, the polymer per se is employed in the hair coloring compositions of the present invention at about 1% to about 4% by weight.

The Polyquaternium 37 polymer component, per the structural formula, is preferred to have a value of about 25 to about 1,000 for n. Thus the molecular weight of the Polyquaternium 37 polymer component is from 5,000 to 210,000. A suitable range for the value of n is about 50 to about 750. A preferred range for the value of n is from 75 to 500 corresponding to a molecular weight of about 15,000 to about 105,000. The preferred anion for X is chlorine such that the polymer component is a quaternary material.

The metal containing pigment of the present invention is typically the component which provides the color to the hair. The metal containing pigment typically contains titanium dioxide or iron oxide. The metal containing pigment is preferably deposited (coated) on mica. A suitable amount of the metal oxide coated mica in the composition of the invention is about 0.5 to 9 percent by weight. Suitable titanium dioxide and iron oxide treated mica products are obtainable from the EM Pigment Division of Rona. Rona is located at 5 Skyline Drive Hawthorne, N.Y. The particle size range for the metal oxide coated mica component is conveniently from about 5 microns to about 150 microns. Preferably, the mean particle size distribution of the metal oxide coated mica component is from about 25 to about 50 microns. The composition of a typical iron oxide coated mica is about 55 to 59% mica and about 41 to 45% iron oxide. The product has a bulk density as measured by a Scott Volumeter of 2.5 to 3.0 grams per cubic inch. The pH of a 10% aqueous suspension of the iron oxide coated mica is from 3 to 6. The product is observed to absorb linseed oil at about 75 g per 100 g of pigment.

A typical mica and titanium dioxide/iron oxide product is from 51 to 61% mica, 34 to 40% titanium dioxide, and 5 to 9% iron oxide. The bulk density of the above product is from 3.0 to 3.5 grams per cubic inch. The pH of a 10% aqueous suspension of the product is about 8.

A suitable amount of cyclomethicone in the composition of the invention is about 0.1 to about 5 percent by weight.

PRODUCT PREPARATION

The product is prepared by combining the various ingredients in a suitable mixing vat. Water is added to the vat and stirring is initiated. The cyclomethicone is added to the water followed by the mica component. The mixing is continued for about one half hour. The Salcare SC 96™ polymer composition is then added to the aqueous mixture and the stirring is continued for about 15 minutes. Any remaining ingredients, including preservatives, fragrances and anti microbial materials may be added at any point in the process where the added ingredient maintains its intended function and where the added ingredient does not interfere with the remainder of the product.

PRODUCT UTILIZATION

The product is applied to clean hair, preferably following a thorough cleansing of the hair. For the best results it is suggested that the hair be wet when the product is applied. Suitable surfactants (detergents) for cleaning the hair prior to applying the composition of the present invention are described below. The same surfactant materials will remove the hair coloring thus rendering the use of the product temporary.

Suitable anionic surfactants are those generally incorporated into a shampoo product. Generally, the anionic surfactant is a water-soluble alkyl or alkyl aryl sulfonate having from about 8 to about 22 carbons, preferably from about 12 to about 18 carbons, in the alkyl radical, which may be straight or branched chain, and also includes such classes of compounds ethoxylated with from 1 to 5 mols, preferably 1 to 3 mols, ethylene oxide per molecule. The sulfate or sulfonate group is typically base-neutralized to provide an alkali metal, especially sodium or potassium, ammonium, or mono, di-, or trialkanolium cation.

Illustrative anionic surfactants of the above-named classes include: Sodium cetyl sulfate, sodium myristyl sulfate, sodium lauryl sulfate, sodium tallow sulfate, sodium decyl sulfate, sodium decylbenzene sulfonate, sodium tridecylbenzene sulfonate, sodium C 14 to C 16 olefin sulfonate, sodium C 12 to C 15 alcohol sulfate, sodium lauryl ether sulfate, sodium myristyl ether sulfate, sodium polyoxyethylene (5 mols ethylene oxide) lauryl ether sulfate, sodium polyoxyethylene (12 mols ethylene oxide) lauryl ether sulfate, sodium nonylphenyl ether sulfate, sodium polyoxyethylene (1 to 4 mols ethylene oxide), C 12 to C 15 alkyl ether sulfate, sodium lauryl sulfoacetate.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight C 12-13 compounds; from 60 to 100% by weight of C 14-15-16 compounds, from about 0 to 20% by weight of C 17-18-19 compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Other suitable anionic detergents utilizable herein are olefin sulfonates having about 12 to about 24 carbon atoms.

The term "olefin sulfonates" is used herein to mean compounds which can be produced by the sulfonation of an alpha-olefin by means of uncomplexed sulfur trioxide, followed by neutralization of the acid reaction mixture in conditions such that any sultones which have been formed in the reaction are hydrolyzed to give the corresponding hydroxy-alkane sulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefin from which the olefin sulfonates are derived are mono-olefin having 12 to 24 carbon atoms, preferably 14 to 16 carbon atoms. Preferably, they are straight chain olefin. Examples of suitable 1-olefin include 1-dodecene; 1-tetradecene; 1-hexadecene; 1-octadecene; 1-cicosene and 1-tetraeosene.

Additional surfactant materials which may be utilized herein include the following exemplified materials. Long Chain tertiary amine oxides corresponding to the following general formula:

$$R^1R^2R^3NO$$

wherein $R^1$ contains an alkyl, alkenyl or monohydroxy alkyl radical of from about 8 to about 18 carbon atoms, from 0 to about 10 ethylene oxide moieties, and from 0 to 1 glyceryl moiety, and $R^2$ and $R^3$ contain from 1 to about 3 carbon atoms and from 0 to about 1 hydroxy group, e.g., methyl, ethyl, propyl, hydroxy ethyl, or hydroxy propyl radicals. The arrow in the formula is omitted as it is a conventional representation of a semi-polar bond between the nitrogen and the oxygen.

Examples of amine oxides suitable for use in this invention include dimethyldodecyl-amine oxide, oleyldi(2-hydroxyethyl)amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, and dimethyl-hexadecylamine oxide.

Further additional surfactants include long chain tertiary phosphine oxides corresponding to the following general formula:

$$RR'R''PO$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and r' and r'' are each alkyl or monohydroxyalkyl groups containing from 1 to 3 carbon atoms. The arrow in the formula is omitted as it is a conventional representation of a semi-polar bond between the phosphorus and the oxygen.

The hair coloring formulation is added to the hair, and thoroughly worked into the hair by the consumer. The level of application of the product is such that the polymer, to the weight of the dry hair treated is about 0.01 to 0.75 grams per gram of hair. Unlike other coloring formulations it is not necessary to rinse the consumer's hair after applying the product.

The product is conveniently applied to the hair at room temperature to slightly elevated temperatures, e.g. 18 to 38 degrees Celsius. As the product has a viscosity of about 130,000 c. p. s., it will be applied as a thick liquid. Thus, the product, is not particularly prone to spillage if dropped by the consumer.

If desired, the new color tint of the hair may be retained by first applying the hair coloring composition of the invention and thereafter applying a fixative hair spray. Suitable fixative hair sprays include PVM MA (polyvinyl methacrylate maleic anhydride copolymer) in SD 40 alcohol. The color will be retained longer by the use of a fixative hair spray as the color is then more resistant to brushing out of the hair color.

OPTIONAL INGREDIENTS

The products described herein can contain a variety of nonessential optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea.

Further optional ingredients include conditioning agents such as cationic surfactants. Examples of cationic surfactants include tricetyl methyl ammonium chloride, cetyl trimethyl ammonium chloride, stearyldimethyl benzyl ammonium chloride, and di-(partially hydrogenated tallow) dimethylammonium chloride. The hair coloring compositions of the present invention to the hair is compatible with a conditioning agent.

Additional ingredients include thickeners and viscosity modifiers such as a diethanolamide of a long chain fatty acid (e.g., PEG 3 lauramide) cocomonoethanolamide, amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

What follows is an example of the preparation of the composition of the present invention:

EXAMPLE I

The composition of the present invention is prepared by adding deionized water to a mixing vat. Mixing is initiated, and cyclomethicone is added at 0.5 parts by weight. Thereafter, a metal oxide coated mica pigment is added at 2.5 parts by weight. Mixing is continued until the pigment is fully dispersed with water and the cymethicone, e. g. the mixing is continued for about one half hour.

The Salcare SC 96™ polymer composition at 2.5 parts by weight is then added to the aqueous mixture and the stirring is continued for about 15 minutes.

The entire process is conducted such that the temperature is maintained at 32 degrees Celsius until the mixing is complete.

The product may also have added a hydantoin preservative at 0.4 parts by weight; tetrasodium ethylene diamine tetraacetate at 0.13 parts by weight; and benzophenone-4 at 0.05 parts. The formulation is at 100 parts by the original addition of deionized water.

The products of the present invention have the advantage of temporarily changing the hair color without chemically damaging the hair in the manner in which bleaching changes the hair. The pilling observed in earlier hair care formulations is avoided.

As the product is temporary in nature it may be utilized for selectively treating portions of the hair such as bangs or the temples with out the risk of over doing the treatment area on a permanent basis. As the method of use of the product utilizes largely inorganic components and significantly avoids skin contact there is no need for skin patch tests as with chemical products.

Having described the invention, the following is claimed:

1. A composition for temporarily coloring hair comprising:
   a. from about 0.5 to about 5 percent by weight of a polymer having repeating units of:
   $\{-CH_2(CH_3)C[CO_2(CH_2)_2N^+(CH_3)_3Cl^-]-\}_n$; and,
   b. from about 0.5 to 9 percent by weight of a metal oxide coated mica where the metal source is a member selected from the group consisting of iron and titanium provided further that the metal oxide coated mica has a mean particle size distribution of about 5 to about 100 microns,
   c. from about 0.1 to 5 percent by weight of cyclomethicone; and,
   d. water; and,
   provided further n has a value of about 25 to 1,000.

2. The composition of claim 1 wherein n has a value of about 50 to about 750.

3. The composition of claim 1 wherein the metal oxide coated mica has a mean particle size distribution of about 5 to about 100 microns.

4. The composition of claim 1 wherein the metal oxide coated mica has a mean particle size distribution of about 25 to about 50 microns.

5. The composition of claim 1 wherein n has a value of about 75 to about 500.

* * * * *